(12) United States Patent
Strobel et al.

(10) Patent No.: US 7,070,985 B2
(45) Date of Patent: Jul. 4, 2006

(54) **APPLICATION OF VOLATILE ANTIBIOTICS AND NON-VOLATILE INHIBITORS FROM *MUSCODOR* SPP. TO CONTROL HARMFUL MICROBES IN HUMAN AND ANIMAL WASTES**

(75) Inventors: Gary Allan Strobel, Bozeman, MT (US); David Ezra, Bozeman, MT (US)

(73) Assignee: Montana State University, Bozeman, MT (US)

( * ) Notice: Subject to any disclaimer, the term of this patent is extended or adjusted under 35 U.S.C. 154(b) by 413 days.

(21) Appl. No.: 10/408,209

(22) Filed: Apr. 4, 2003

(65) Prior Publication Data

US 2004/0018168 A1 Jan. 29, 2004

Related U.S. Application Data

(63) Continuation-in-part of application No. 10/121,740, filed on Apr. 11, 2002, now Pat. No. 6,911,338.

(60) Provisional application No. 60/363,072, filed on Mar. 11, 2002, provisional application No. 60/283,902, filed on Apr. 16, 2001.

(51) Int. Cl.
*B09B 3/00* (2006.01)

(52) U.S. Cl. .................................. 435/262.5; 435/252.4

(58) Field of Classification Search .................... None
See application file for complete search history.

(56) References Cited

OTHER PUBLICATIONS

C. W. Bacon & J.F. White Jr., An Overview of Endophytic Microbes: Endophytism Defined, Microbial Endophytes, Feb. 25, 2000, p. 1-21, vol. N/A, Marcel Dekker, Inc., New York, NY United States of America.
J. Bjurman & J. Kristensson, Volatile production by *Aspergillus versicolor* as a possible cause of odor in houses affected by fungi, Mycopathologia, 1992, pp. 173-178, vol. 118, Kluwer Academic Publishers, Dordrecht Netherlands.
J.Y. Li, & G.A. Strobel, Jesterone and hydroxy-jesterone antioomycete cyclohexenone expoxides from the endophytic fungas *Pestalotiopsis jesteri*, Phytochemistry, 2001a, pp. 261-265, vol. 57, Elsevier Science (US), New York, NY United States of America.
J.Y. Li, J. Harper, D.M. Grant, B.O. Tombe, B. Bashyal, W.M. Hess, G.A. Strobel, Cambuic acid, a highly functionalized cyclohexenone with antifungal activity from *Pestalotiopsis* spp and *Monochaetia* sp., Phytochemistry, 2001b, pp. 463-468, vol. 56, Elsevier Science (US), New York, NY United States of America.

J.Y. Li, G.A. Strobel, J. Harper, E. Lobkovsky, & J. Clardy, Cryptocin, a potent tetramic acid antimycotoc from the endophytic fungus *Cryptosporiopsis cf. quercina*, Organic Letters, 2000, pp. 767-770, vol. 2, American Chemical Society, Columbus, OH United States of America.
S. Rapior, F. Fons, & J. Bessiere, The fenugreek odor of *Lactarius helvius*, Mycologia, 2000, pp. 305-308, vol. 92, Allen Press, Inc., Lawrence, KS United States of America.
J. Schnurer, J. Olsson & T. Borjesson, Fungal volatiles as indicators of food and feeds spoilage., Fungal Genetics and Biology, 1999, pp. 209-217, vol. 27, Academic Press, San Diego, CA United States of America.
A. Stierle, G.A. Strobel, & D. Stierle, Taxol and taxane production by *Taxomyces andreanae*, and endophytic fungas of Pacific yew., Science, 1993, pp. 214-216, vol. 260, American Association for the Advancement of Science, Washington, D.C., United States of America.
G.A. Strobel, J.Y. Li, F. Sugawara, H. Koshino, J. Harper, & W.M. Hess, OocydinA, a chlorinated macrocyclic lactone with potent ant-oomycete activity from *Serratia marcescens.*, Microbiol, 1999, pp. 3557-3564, vol. 145, Society for General Microbiology, Spencer Wood, Reading, UK.
G.A. Strobel, E. Dirksie, J. Sears, & C. Markworth, Volatile antimicrobials from a novel endophytic fungas., Microbiol, 2001, pp. 2943-2950, vol. 147, Society for General Microbiology, Spencer Wood, Reading, UK.
J. Woropong, G.A. Strobel, E.J. Ford, J.Y. Li, G. Baird, & W.M. Hess, *Muscodor roseus* aman. nov. an endophyte from *Cinnamonum zeylanicum.*, Mycotaxon, 2001, pp. 67-79, vol. 79, Mycotaxon, LTD, Ithica, NY United States of America.
J. Woropong, G.A. Strobel, B. Daisy, U.F. Castillo, G. Baird, & W.M. Hess, *Muscodor roseus* aman. nov. an endophyte from *Grevvillea pteridifolia.*, Mycotaxon, 2002, pp. 463-475, vol. 80, Mycotaxon, LTD, Ithica, NY United States of America.

*Primary Examiner*—Irene Marx
(74) *Attorney, Agent, or Firm*—Antoinette M. Tease

(57) ABSTRACT

This invention relates to the discovery of a novel endophytic fungus, *Muscodor albus*, which produces volatile antibiotics that have been shown to be effective in the treatment of human and animal waste products. Through experimentation, this invention confirms that *Muscodor albus* can be used in disposable bags in connection with portable toilets to solve the problem of degradation of waste products in situations where humans are removed from sanitary facilities. This invention includes the discovery of non-volatile inhibitors that are also produced by *Muscodor albus* and that are similarly effective in treating human and animal wastes. This invention covers a unique and novel method for preparing *Muscodor albus* for commercial use in the treatment of human and animal wastes, which involves infesting barley seeds with *Muscodor albus* and then storing them under conditions that will allow the fungus to remain viable for up to nine months.

12 Claims, 10 Drawing Sheets

APPLICATION OF VOLATILE ANTIBIOTICS AND NON-VOLATILE INHIBITORS FROM *MUSCODOR* SPP. TO CONTROL HARMFUL MICROBES IN HUMAN AND ANIMAL WASTES

CROSS-REFERENCE TO RELATED APPLICATIONS

This application claims the benefit under 35 U.S.C. § 120 and is a continuation-in-part of U.S. Nonprovisional application Ser. No. 10/121,740, filed Apr. 11, 2002, now U.S. Pat. No. 6,911,338 which in turn claims the benefit under 35 U.S.C. § 119(e) of U.S. Provisional Application No. 60/283,902, filed Apr. 16, 2001 and of U.S. Provisional Application No. 60/363,072, filed Mar. 11, 2002. The contents of these applications are hereby incorporated by reference into the present disclosure.

BACKGROUND OF THE INVENTION

Throughout this application, various articles and books are referenced by authorship and date. The full bibliographic citation for each publication can be found at the end of the specification, immediately preceding the claims. In addition, certain terms used in this application are defined in the definitions section immediately following the references.

The present invention relates to the discovery of a novel endohpytic fungus, *Muscodor albus* (*M. albus*), that makes a series of volatile compounds that are inhibitory and/or lethal to other microbes including those found in human wastes such as *Escherichia coli* (*E. coli*) and *Vibrio cholerae*. In a preferred embodiment, the gas phase of these novel fungi, including *M. albus* and fungi related to it such as *Muscodor roseus* (*M. roseus*), are used in the treatment of human wastes, and in particular, those contained in the WAG BAG™ (defined below). The volatile gases of *M. albus* consist of at least 28 compounds, most of which have been identified. An artificial mixture of these compounds, in the gas phase, largely mimics the effects of the fungal gases relative to their bioactivity (Strobel et al., 2001). The present invention also relates to the preparation, growth, formulation and storage of the *M. albus* so that it can ultimately placed into the WAG BAG™ or similar bags used in connection with portable toilets and effectively be wetted by human urine and begin to make its gases and inhibit and kill harmful microorganisms found in human wastes.

Figure 1:

This invention addresses several extremely important developments that relate to modern concerns and needs for the safe and effective treatment of liquid and solid human wastes. This need arises especially with respect to people who are removed, from one reason or another, from sanitary facilities. This may include those who are serving in defense forces in the field or in a recreational mode. It may include people who are in emergency or natural disaster situations, or in conditions of national war or other political disasters. In each of these situations, in order to survive, the human body needs to effectively pass liquid and solid wastes. Unfortunately, in many cases, both environmental as well health hazards are caused when these wastes are not properly disposed (FIG. 1). It is for these reasons that Phillips Environmental Products, Inc. has developed a biodegradable WAG BAG™ for use in connection with the Portable Environmental Toilet (PETT®) (U.S. Pat. No. 6,341,386). The WAG BAG™ contains an agent that absorbs and gels liquid, and upon burial or proper disposal, will degrade into harmless organic material. What is needed is a method to immediately treat the wastes so that in the first ten days to two weeks after collection in the bag there is an effective reduction of the majority of harmful bacterial organisms, followed by degradation of the dead bacteria and unprocessed polymers such as cellulose, hemicellulose and lignins contained in the human solid waste. The application of *M. albus* in a form that can be placed in the WAG BAG™ is also critical to the treatment processes. Data supporting this treatment process via the use of *M. albus* are included in this patent application.

*M. albus* was isolated as an endophytic fungus growing within the limb tissues of *Cinnamomum zeylanicum* in the Caribbean rainforest of Honduras in 1997 (Strobel et al., 2001). Endophytes have been classified as microbes living within the living tissues of host plants without causing any overt symptoms of disease or other harm (Bacon and White, 2000). *M. albus* produced no spores in culture, and thus it had to be classified primarily according to its molecular biological characteristics (Woropong et al., 2001). This endophytic microbe is of the xylariaceae family. It has a close relative, *M. roseus*, which also makes volatile antibiotics (Woropong et al., 2002). When *M. albus* was originally isolated, it was noted that it killed all other microbes that were also emerging from the cinnamon tree limbs that were in culture. This was a significant observation because it showed that the fungus was making gaseous compounds that were lethal to other microbes, in other words, volatile antimicrobials. This observation appears to be the first time that anyone has noticed such a phenomenon from an endophytic microbe, although others have noted the fact that fungi produce odors, but not with lethal microbial effects (Bjurman and Kristensson, 1992; Dennis and Webster, 1971; Rapior et al., 2000 and Schnurer et al., 1999).

Thus it was necessary to trap and identify the individual compounds produced by this fungus and then mimic the effects in a similar manner. It was also necessary to devise a bioassay test and to determine the microbes and other organisms that may be sensitive to the effect of these fungal gaseous compounds. It was learned that the gases are lethal or inhibitory to many human pathogenic fungi and bacteria, including, but not limited to, *E. coli, Vibrio cholerea, Candida albicans* and *Aspergillus fumigatus*. The former two bacteria are found in human wastes and are pathogenic to humans. Usually, only a 24-hour exposure to the fungal gases is required to produce lethal or inhibitory effects. In some instances, however, a longer exposure is required.

This invention also relates to the discovery of several other gas-producing fungi that are also effective in killing other microbes. They were isolated by using *M. albus*, as the source of selective gases, in the presence of plant material suspected of supporting other gas-producing endophytes. It turns out that other fungal relatives in the xylariaceae family are not sensitive to the *M. albus* gases. Thus, the volatile antibiotics selectively eliminate all microbes except its relatives and other volatile antimicrobial producers. At least two other volatile antimicrobial endophytes have been isolated, and they too are effective in killing other microbes. These fungi have been designated as A3-5 and A10-1 (Woropong et al., 2002). They resemble *M. albus* in that they produce antimicrobial volatiles and do not make spores, but the antimicrobial volatiles they produce are not identical to those of *M. albus*. These fungi are called *M. roseus*, and they are as effective as *M. albus* in controlling other microbes (Worapong et al., 2002).

BRIEF SUMMARY OF THE INVENTION

The purpose of the present invention is to illustrate the effectiveness of *M. albus* in the treatment of human and animal wastes. In order for the volatile antibiotics produced by *M. albus* to be effective in treating human and animal wastes, treatment is most effective in a closed environment, such as a disposable bag used in connection with a portable toilet. The preferred embodiment described in this application is the use of *M. albus* in connection with the WAG BAG™, but this invention expressly anticipates the use of *M. albus* in connection with other types of closed environments, as well as non-closed environments, to treat human and animal waste.

This invention includes the discovery that in addition to producing volatile antibiotics, *M. albus* produces non-volatile, water-diffusible substances that inhibit the growth of bacteria. These non-volatile inhibitors do not need to be in a closed environment to be effective. In addition, this invention includes a method for preparing and storing *M. albus* for use in the treatment of human and animal waste products.

BRIEF DESCRIPTION OF THE TABLES AND FIGURES

Table 1. A GC/MS analysis of the compounds present in the volatile fraction of *M. albus* having been grown on potato dextrose broth medium (PDA) (Strobel et al., 2001).

Table 2. A GC/MS analysis of the compounds present in the volatile fraction of liquid and solid human wastes in the presence of *M. albus*. Only signature compounds associated with *M. albus* are shown in the table. These compounds did not appear in the control experiment not having *M. albus* present. Literally tens of other volatile compounds are present in the sealed atmosphere of the human wastes.

FIG. 1. An illustration of the problem of the improper disposal of human solid wastes along the Inca Trail, Peru, in August of 2002.

Figure 2:
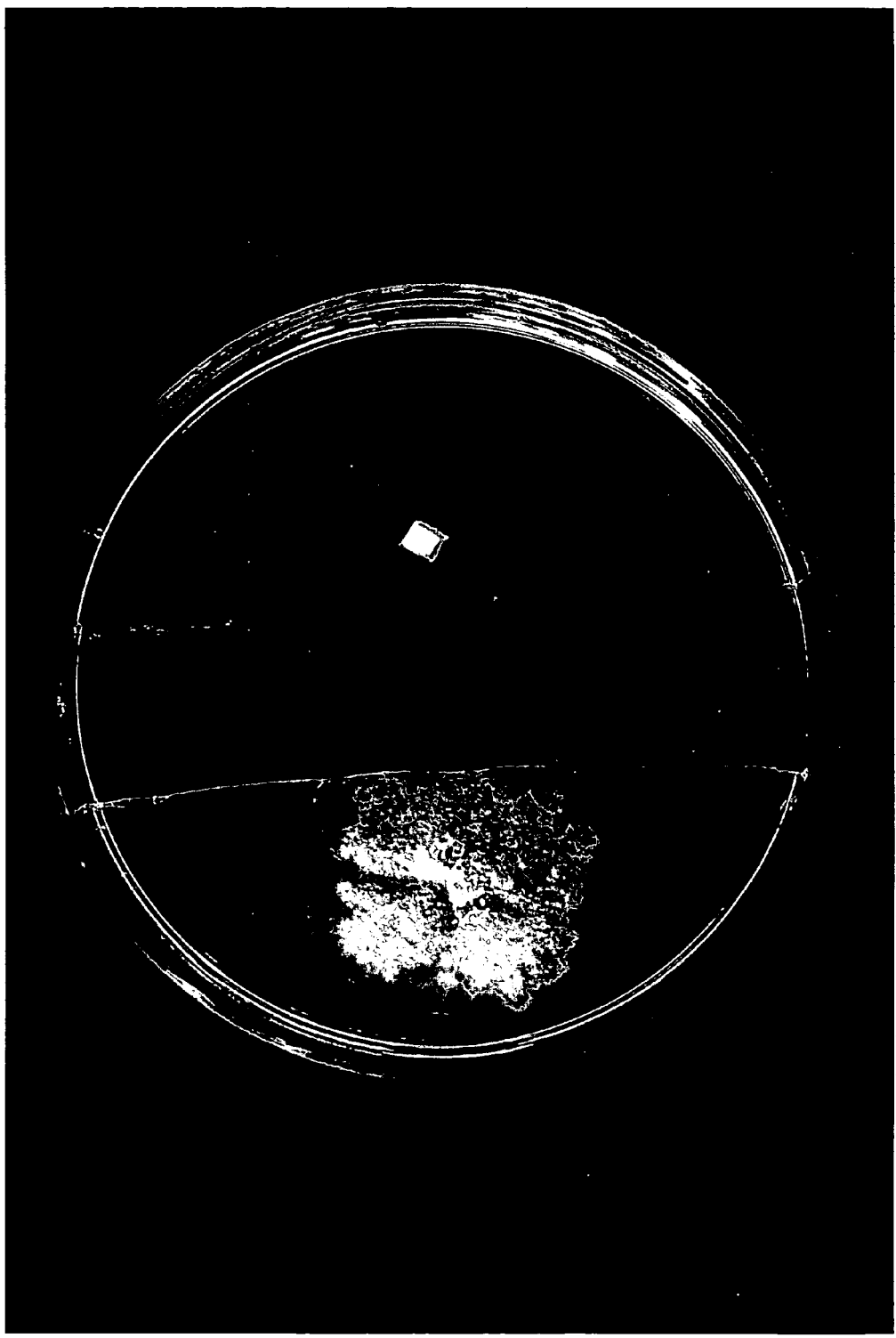

FIG. 2. An illustration of the bioassay used to test and demonstrate that cultures of *M. albus* are making volatile antimicrobial compounds.

Figure 3:
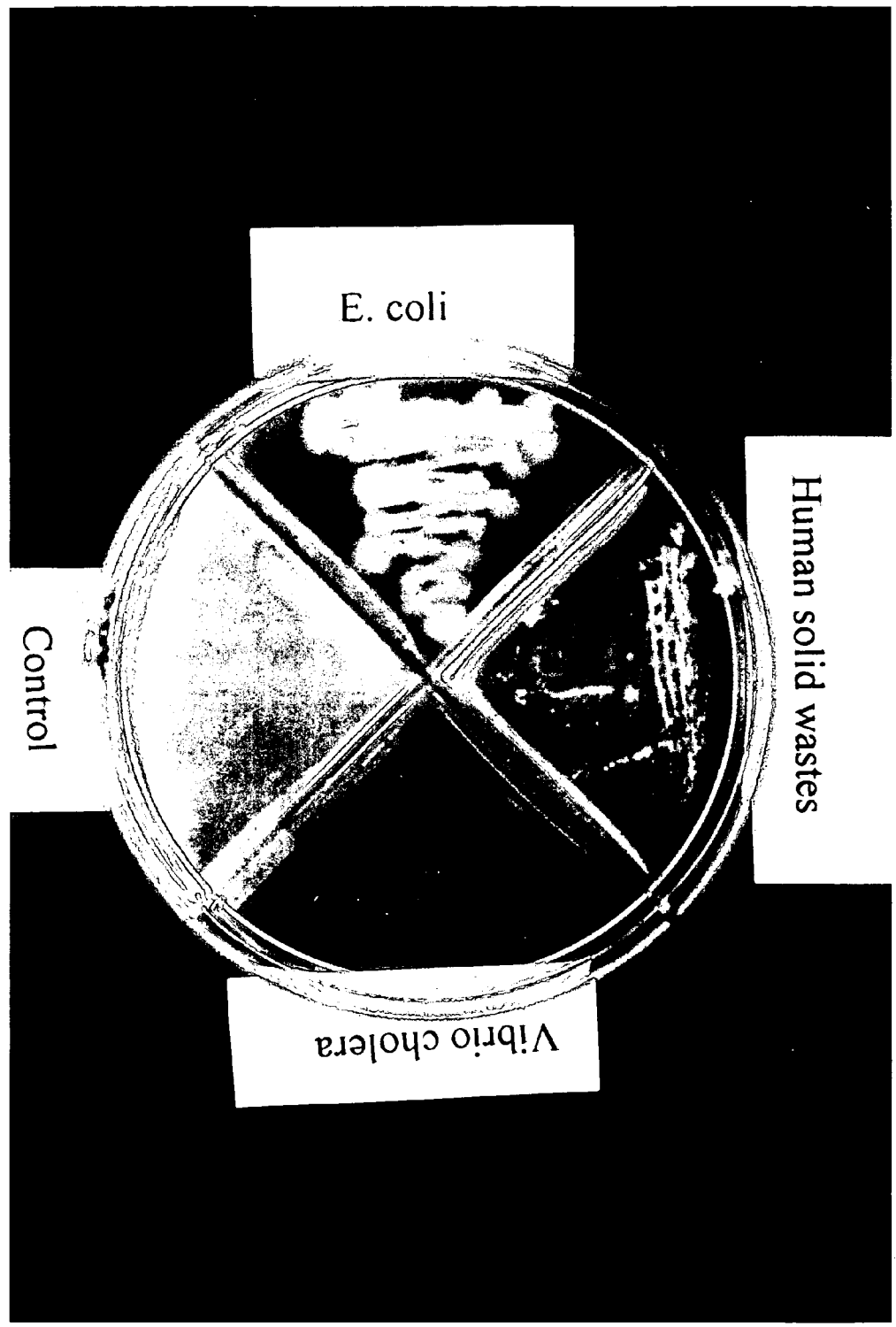

FIG. 3. Inhibition of *E. coli, Vibrio cholerea*, and the normal flora of human solid wastes by *M. albus* after two days exposure to the inhibitory volatiles of this fungus in the quadrant plate bioassay test system.

Figure 4:
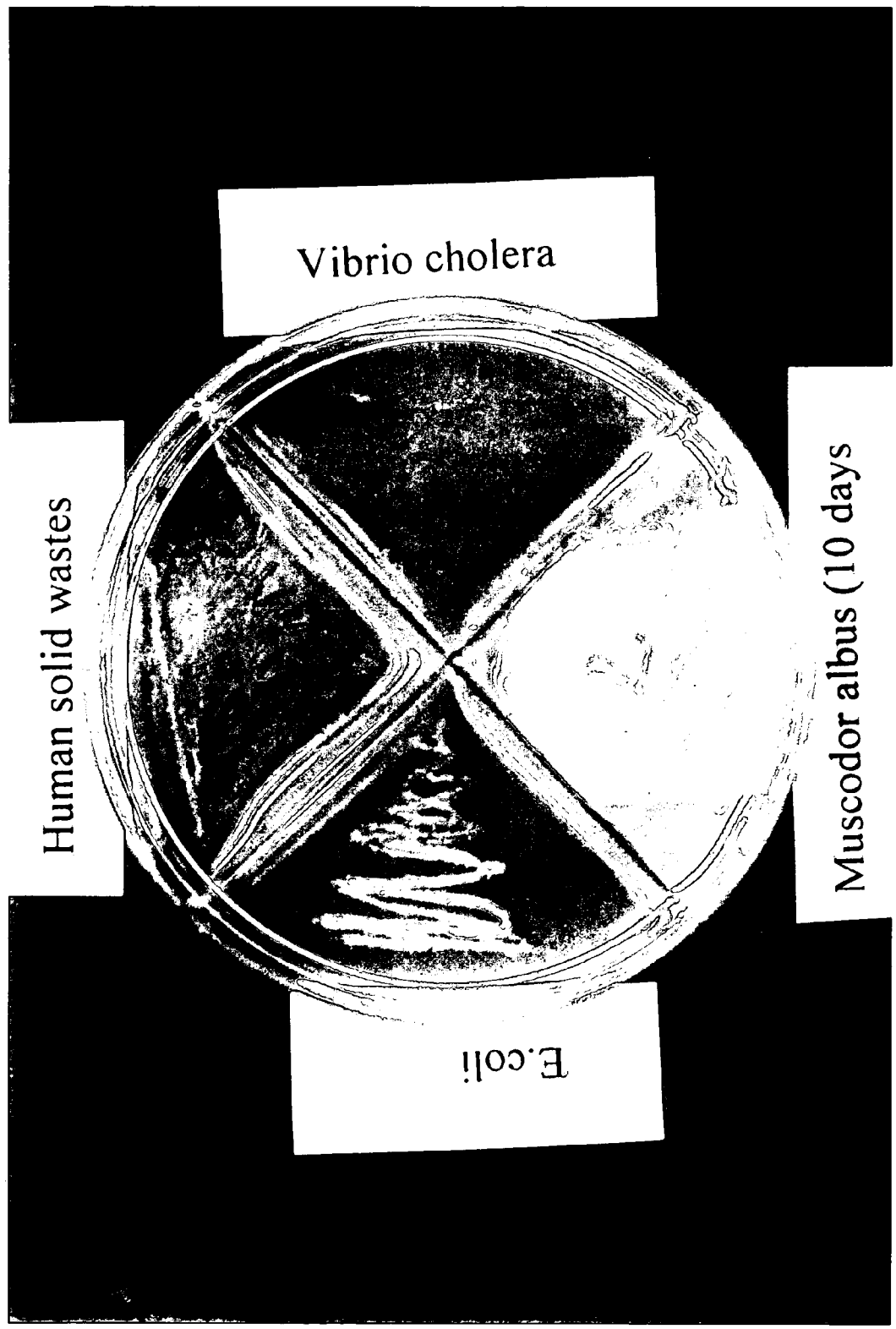

FIG. 4. A control experiment of the one illustrated in FIG. 3 in which *M. albus* was not placed on the four quarter plate and thus all bacteria grew profusely.

Figure 5:
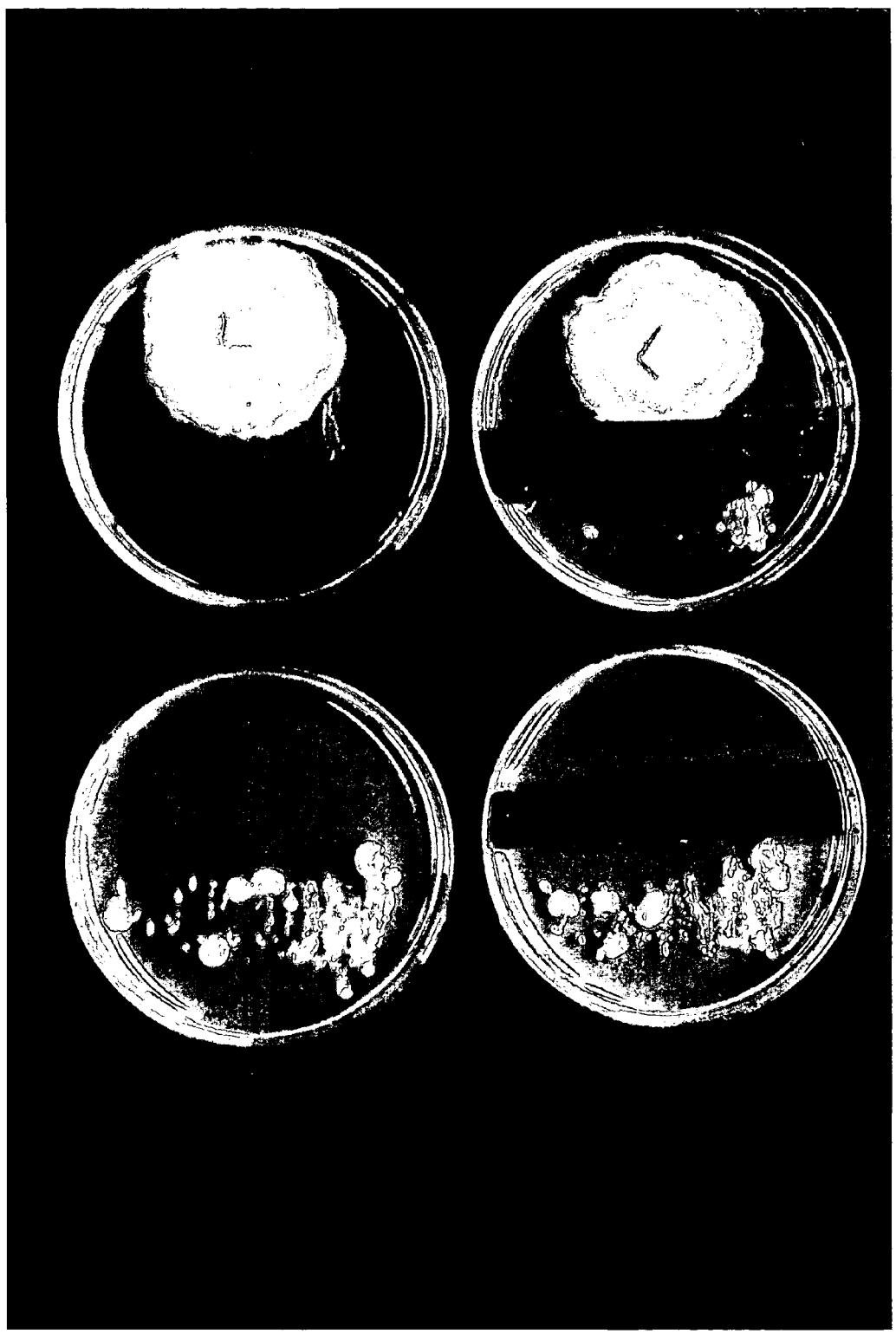

FIG. 5. The split plate agar assay system and the inhibition of bacterial growth from human wastes. The white growth is *M. albus*, and it is on both a split plate and a solid agar (PDA) plate with a streak of human solid wastes (right side of plates). The control plates have no *M. albus* growth, and the bacterial growth from the human excrement is enormous. In the other cases, the *M. albus* does inhibit bacterial growth in human wastes, but the inhibition is greater when the fungus is not on the split plates, which suggests the presence of non-volatile inhibitors.

Figure 6:
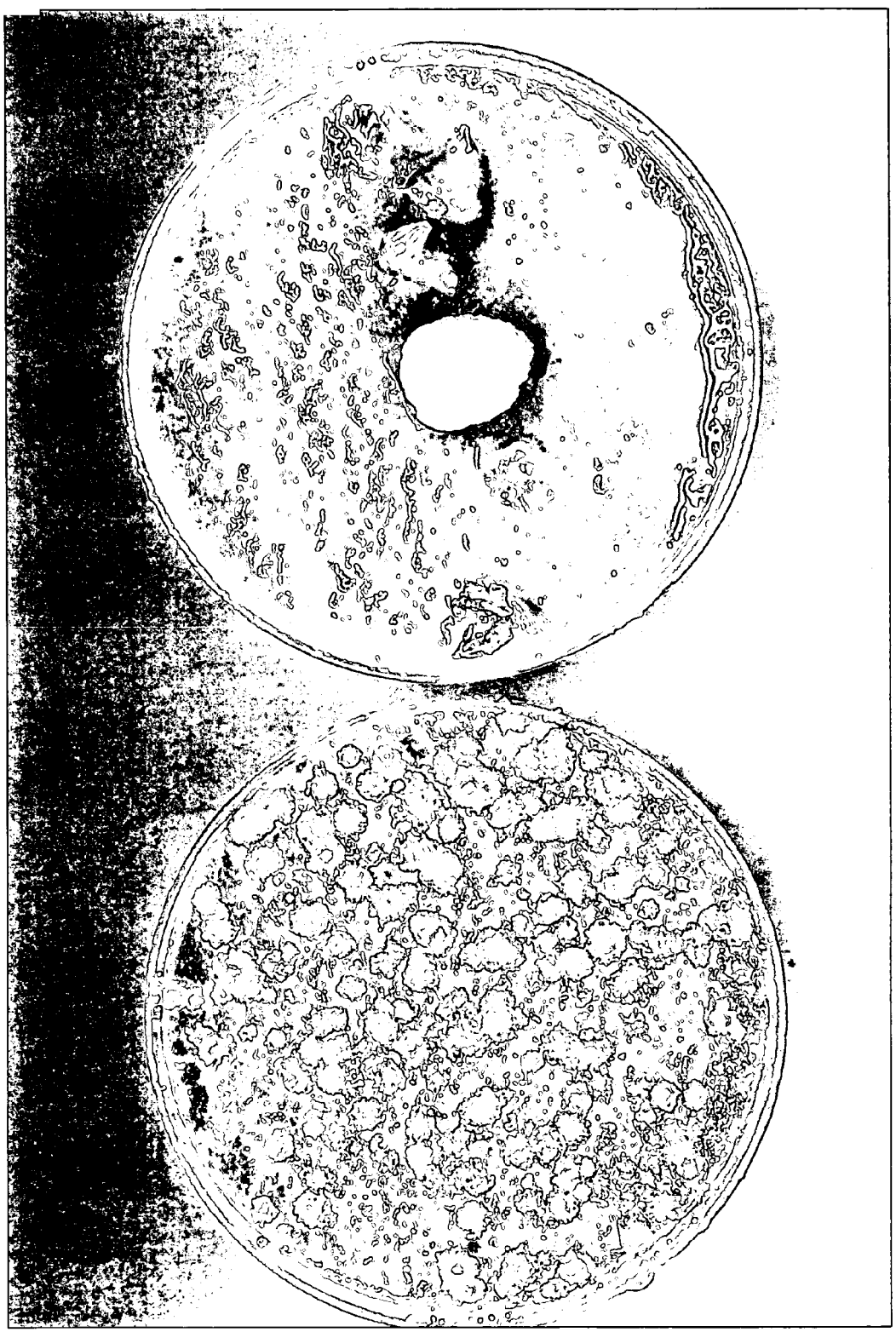

FIG. 6. An experiment to illustrate the fungal inhibitory properties of *M. albus* while growing exclusively in human urine and the acrylamide gelling polymer. See the "Detailed Description of Invention" for details. The *M. albus* (white culture) is on the top. The control culture without *M. albus* is on the bottom and is sporting fungal contamination.

Figure 7:
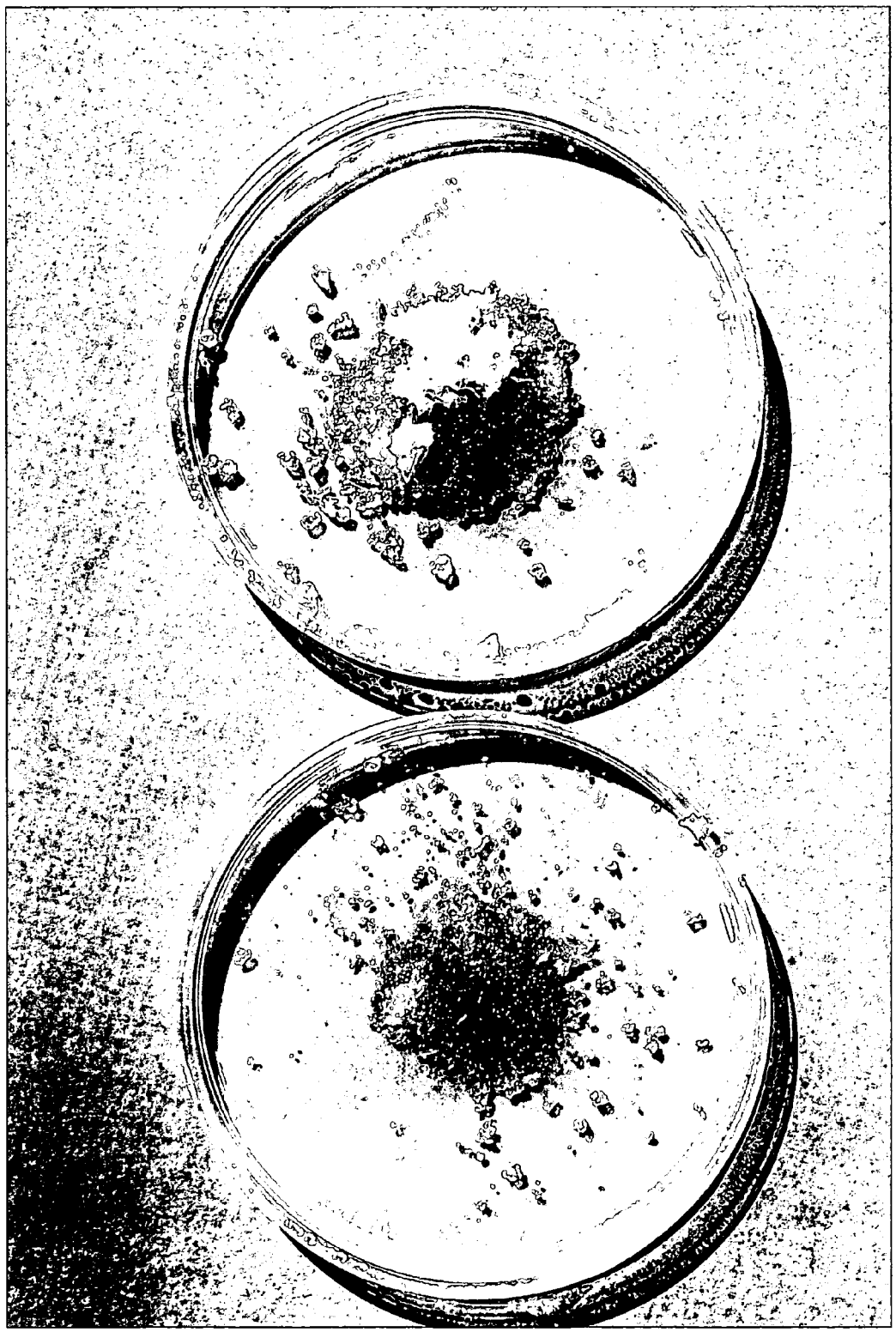

FIG. 7. A critical experiment to show the growth and antimicrobial effects of *M. albus* in the presence of the gelling powder, human solid wastes and urine. GC/MS tests were done to show that certain inhibitory signature gases produced by *M. albus* were present in the atmosphere above the solid and liquid wastes. Samples were taken that showed a marked reduction in the population of microbes in the wastes. See the "Detailed Description of Invention" and Table 2 for details. The top of FIG. 7 is the wastes, gel and *M. albus*, whereas the bottom is the control without the fungus.

Figure 8:

FIG. 8. An SEM (scanning electron micrograph) of the hyphae and ropy mycelium of *M. albus* growing on sterilized plant material (×3500 magnification).

Figure 9:

FIG. 9. A comparable SEM showing the hyphae and ropy mycelium of *M. albus* growing on a barley seed infested with *M. albus* having been recovered from a WAG BAG™ containing solid and liquid human wastes (×2700 magnification).

Figure 10:

FIG. 10. The mycelium of *M. albus* growing on barley seed that will eventually be dried and used for inoculating the WAG BAG™.

TABLE 1

GC/MS analysis of the volatile compounds produced by *M. albus* having been grown on PDA. Several minor peaks and the breakthrough peak were omitted from the total analysis because they represent only 1% of the total area. Compounds found in the control PDA plate are not included in this table.

| RT | Total Area (%) | M/z | Possible compound | MW |
|---|---|---|---|---|
| 3:45 | 0.33 | 114 | Octane | 114 |
| 4:19 | 0.93 | 58 | Acetone | 58 |
| 4:37 | 0.68 | 74 | Methyl acetate | 74 |
| 5:56 | 7.63 | 88 | Ethyl acetate | 88 |
| 6:51 | 0.31 | 102 | Propanoic acid, 2-methyl, methyl ester | 102 |
| 7:16 | 6.24 | * | Ethanol | 46 |
| 8:03 | 2.07 | 116 | Propanoic acid, 2-methyl-ethyl ester | 116 |
| 11:45 | 0.58 | * | Propanoic acid, 2-methyl 2-methylpropyl ester | 144 |
| 12:05 | 2.06 | 74 | Isobutyl alcohol | 74 |
| 12:50 | 22.24 | * | 1-butanol, 3-methyl, acetate | 130 |
| 14:57 | 1.53 | * | Propanoic acid, 2-methyl, 3-methylbutyl ester | 158 |
| 15:28 | 22.99 | * | 1-butanol, 3-methyl- | 88 |
| 16:08 | 0.29 | 138 | #Furan, 2-pentyl- | 138 |
| 18:53 | 0.29 | 142 | #4-nonanone | 142 |
| 20:38 | 0.41 | 142 | 2-nonanone | 142 |
| 21:07 | 0.30 | 204 | #Naphthalene, decahydro-4a-methyl-1-methylene-7-(1-methylethylidene)-, (4aR-trans)- | 204 |
| 22:54 | 1.51 | 204 | # Azulene, 1,2,3,4,5,6,7,8-octahydro-1,4-dimethyl-7-(1-methylethenyl)-,[1S-(1.alpha.,4.alpha.,7.alpha.)] | 204 |
| 23:16 | 0.94 | 204 | # Cyclohexene, 4-(1,5-dimethyl-1,4-hexadienyl)-1-methyl- | 204 |
| 25:20 | 3.63 | 204 | # 1H-3a,7-methanoazulene, 2,3,4,7,8,8a-hexahydro-3,6,8,8 tetramethyl-, [3R-(3.alpha., 3a.beta.,7.beta. ,8a.alpha.)] | 204 |
| 25:30 | 6.08 | 88 | Propanoic acid, 2-methyl | 88 |
| 26:04 | 0.48 | 204 | Caryophyllene | 204 |
| 27:55 | 0.34 | 204 | # Naphthalene,1,2,4a,5,6,8a-hexahydro-4,7-dimethyl-1-(1-methylethyl)-, [1R-(1.alpha., 4a.alpha.,8a.alpha.)] | 204 |
| 28:34 | 0.36 | 204 | # Spiro[5.5]undec-2-ene,3,7,7-trimethyl-11-methylene- | 204 |
| 28:50 | 1.07 | 204 | Azulene,l,2,3,5,6,7,8, 8a-octahydro-1, 4-dimethyl-7-(1-methylethyenyl)-, [1S-(1.alpha.,7.alpha.,8a.beta.)] Common Name: Bulnesene | 204 |

TABLE 1-continued

GC/MS analysis of the volatile compounds produced by *M. albus* having been grown on PDA. Several minor peaks and the breakthrough peak were omitted from the total analysis because they represent only 1% of the total area. Compounds found in the control PDA plate are not included in this table.

| RT | Total Area (%) | M/z | Possible compound | MW |
|---|---|---|---|---|
| 28:57 | 3.24 | 204 | Naphthalene, 1,2,3,5,6,7,8,8a-octahydro-1,8a-dimethyl-7-(1-methylethenyl)-,[1R-(1.alpha.,7.beta.,8a.alpha.)] Common Name: Valencene | 204 |
| 31:12 | 1.74 | * | Acetic acid,2-phenylethyl ester | 164 |
| 33:17 | 1.06 | 122 | Phenylethyl alcohol | 122 |
| 39:00 | 9.76 | 204 | # Unknown | 204 |

*No molecular-ion peak was observed in the spectrum of either the standard compound or the compound undergoing the analysis.
Denotes that a spectrum and retention time of this component was observed and the substance matched to the most likely compound in the NIST database, but the data have not been confirmed by use of an appropriate identical standard compound by either retention time or MS. These compounds were not placed in the artificial mixture in the bioassay test.

TABLE 2

GC/MS analysis of the volatile compounds produced by *M. albus* having been grown on solid as well as liquid human wastes in the presence of the acrylamide polymer. The table displays those compounds that were present in the plate containing *M. albus* and that were not found in the control plate. The myriad of other volatile compounds present in both the treatment plate and the control plate are not shown in this document.

| RT | Total Area (%) | M/z | Possible compound | MW |
|---|---|---|---|---|
| 4:44 | 0.25 | 88 | Ethyl acetate | 88 |
| 11:00 | 2.23 | * | 1-butanol, 3-methyl, acetate | 130 |
| 13:37 | 13.18 | * | 1-butanol, 3-methyl- | 88 |
| 18:14 | 0.29 | * | Propanoic acid, 2-methyl, propyl ester | 130 |
| 23:18 | 1.85 | 88 | Propanoic acid, 2-methyl | 88 |
| 29:30 | 1.50 | * | Acetic acid, 2-phenylethyl ester | 164 |
| 31:32 | 1.41 | 122 | Phenylethyl alcohol | 122 |

*No molecular-ion peak was observed in the spectrum of either the standard compound or the compound undergoing the analysis.

DETAILED DESCRIPTION OF THE INVENTION

The *Muscodor* spp. described in this invention are the first of their type ever to be isolated in nature. They are found as endophytes in certain plants growing in Central and South America and Australia. Certain of these *Muscodor* spp. produce volatile antibiotics, and these antibiotics have proven useful in controlling certain unwanted microbes. Every part of the planet inhabited by humans has problems dealing effectively with the disposal of solid and liquid wastes that are engorged with various bacteria and fungi. These microbes have disease-causing potential and, therefore, need to be controlled and properly disposed of. This document shows, with appropriate experimentation, that *Muscodor albus* can be grown under controlled laboratory conditions and then applied to human wastes in the conditions that mimic the WAG BAG™ and produce a reduction in the numbers of bacteria that normally inhabit human wastes. The volatile antimicrobial compounds commonly produced by this organism in culture are also produced in the presence of human wastes. Bacteria and fungal growth are both inhibited in human wastes under these conditions. Shown below is a logical sequence of examples of how this important biological process can function to reduce microbial populations in human wastes.

The organism was initially isolated as an endophyte from a Cinnamon tree in Honduras (Strobel et al., 2001). It was previously shown to make volatile antibiotics, and certain aspects of its utility were the subject of both provisional and nonprovisional patent applications (see Cross-Reference to Related Applications). We now wish to expand on the details of the utility of this organism in treating both liquid and solid human wastes to help reduce the populations of harmful bacteria and fungi contained therein. It is worth noting that the gases produced by *M. albus* kill *E. coli* and other microbes found in all solid mammalian wastes. Thus, *M. albus* cultures can be used to decontaminate fecal matter of all animal origins. Similarly, *M. albus* cultures can be used to rid animal as well as human urine of fungal contamination.

A. EXAMPLE 1

Analysis of the Volatiles of *M. albus*

A method was devised to analyze the gases in the air space above the *M. albus* mycelium growing in Petri plates. First, a "Solid Phase Micro Extraction" syringe was shown to be a convenient method for trapping the fungal volatiles. The fiber material (Supelco) was 50/30 divinylbenzene/carburen on polydimethylsiloxane on a stable flex fiber. The syringe was placed through a small hole drilled in the side of the Petri plate and exposed to the vapor phase for 45 minutes. The syringe was then inserted into a gas chromatograph (Hewlett Packard 5890 Series II Plus) equipped with a mass-selective detector. A 30 m×0.25 mm I.D. ZB Wax capillary column with a film thickness of 0.50 mm was used for the separation of the volatiles. The column was temperature programmed as follows: 25° C. for 2 minutes followed to 220° C. at 5° C./minute. The carrier gas was Helium Ultra High Purity (local distributor), and the initial column head pressure was 50 kPa. The He pressure was ramped with the temperature ramp of the oven to maintain a constant carrier gas flow velocity during the course of the separation. Prior to trapping the volatiles, the fiber was conditioned at 240° C. for 20 minutes under a flow of helium gas. A 30-second injection time was used to introduce the sample fiber into the GC. The gas chromatograph was interfaced to a VG 70E-HF double focusing magnetic mass spectrometer operating at a mass resolution of 1500. The MS was scanned at a rate of 0.50 seconds per mass decade over a mass range of 35–360 amu. Data acquisition and data processing were performed on the VG SIOS/OPUS interface and software package. Initial identification of the unknowns produced by *M. albus* was made through library comparison using the NIST database.

Comparable analyses were conducted on Petri plates containing only PDA, and the compounds obtained therefrom (mostly styrene) were subtracted from the analyses done on plates containing the fungus. Final identification of 20/28 compounds was done on a comparative basis to authentic standards using the GC/MS methods described above. However, eight other compounds composing only approximately 20% of the volatiles have been tentatively identified on the basis of the NIST database information and were not included in any of the bioassay tests that employed artificial mixtures of *M. albus* compounds.

As a first approximation, the quantitative analysis of each compound found in fungal cultures is based on its relative peak area obtained after GC-MS analysis (Table 1) (Strobel et al., 2001). Details on the bioactivity of each compound and mixtures of these compounds are to be found in the Strobel et al. (2001) reference.

B. EXAMPLE 2

Bioassay of *M. albus* Against Human Pathogens

A relatively simple bioassay test system was devised that allows only for volatiles being the causative agents for any microbial inhibition. Initially, on a Petri plate with PDA, an agar strip 2.5 cm wide was completely removed from the mid-portion of it (FIG. 2). Then, *M. albus* was inoculated and grown on one side of the plate for varying time periods prior to testing. The test fungus or bacterium was placed onto the agar half moon strip on the opposite side of the plate. Individual fungi were inoculated on the test side of the plate on a 3 mm$^3$ plug of agar. Bacteria and *Candida albicans* were simply streaked (1.5 cm long) onto the PDA on the test side of the plate. The act of removing a strip of agar from the mid-portion of the plate effectively precluded the diffusion of any inhibitory soluble compounds emanating from *M. albus* to the fungi or bacteria being tested (FIG. 2). The plate was wrapped with two individual pieces of parafilm and incubated at 23° C. The growth of these latter organisms was visually judged on the basis of any new microbial density appearing on the area of the agar that had been inoculated. Eventually the viability of each test fungus and bacterium was evaluated. The latter was done for each test microorganism by either removing the agar plug, containing the test fungus and placing it onto a PDA-Petri plate, or re-streaking the test bacterium or yeast from the original test streak made on the test side of the plate. Each bacterium and fungus was subjected to testing at the point that it was producing fresh growth. In addition, appropriate control experiments were conducted in which the test fungus or bacterium was subjected to the same procedures minus *M. albus* on the test side of the Petri plate. In each case, appropriate growth and viability of each organism was noted in the experimental setup. It should be noted that while PDA is not the most ideal medium for the bacteria and human pathogenic fungi used in this study, it did satisfactorily support the growth of these organisms. Its use, while adequately supporting the growth of *M. albus*, also precluded the need to pour other agar into the other half of the Petri plate to support the growth of the test fungus or bacterium.

In another version of the test, a Petri plate organized in quarters (plastic dams) has *M. albus* inoculated into one quadrant and test organisms in the other quadrants. After a few days growth on the *M. albus* quadrant, the various test organisms were then applied to the other quadrants. Little or no bacterial growth appeared in the quadrant with solid human wastes. Similarly, little or no growth appeared with *Vibrio cholerea*, and there was inhibition of the growth of *E. coli*. The quadrants supporting bacterial growth were on the Milton-Hinton agar, whereas the fungus was supported on PDA. The growth observations were made after two days at 23° C. (FIG. 3). In contrast, the control plate having no *M. albus* culture produced ample bacterial growth in each quadrant including the one with the streak of solid human waste (FIG. 4).

C. EXAMPLE 3

Direct Petri Plate Inhibition Assays

While the quadrant plate technique unequivocally demonstrated that volatiles diffusing from *M. albus* were inhibitory to microbes found in human wastes such as *E. coli* and *Vibrio cholerea*, evidence of other inhibitory compounds in *M. albus* was sought. To this end, ten-day-old cultures of *M. albus* on half plates, with and without the center strip removed (known as a split plate), were incubated with streaks of human solid wastes for seven days. Appropriate controls, without *M. albus*, were also run simultaneously. The results showed that virtually no bacterial growth occurred on the plate with *M. albus*, the human wastes, and no removal of the agar strip. Likewise, some inhibition occurred on the plate with *M. albus*, human wastes, and the agar strip removed, which suggests that the volatiles of *M. albus* were affecting bacterial growth but not as extensively as when direct contact of the wastes and the fungal culture existed. As expected, in the controls, bacteria growth was extensive and covered the entire side of the plate that was streaked with the wastes (FIG. 5) in both the split plate as well as in an intact plate. These results suggest that, in addition to the antibiotic volatiles made by *M. albus*, there are also one or more diffusible substances produced by *M. albus* that are inhibitory to bacteria found in human wastes (FIG. 5). Ultimately, *M. albus* is inhibitory to the bacteria in human wastes by virtue of both volatile as well as water diffusible (non-volatile) substances.

D. EXAMPLE 4

Inhibition of Fungal Growth in Human Urine

While fungal growth in general is killed or inhibited by *M. albus*, it was of interest to determine if *M. albus* was inhibitory to general fungal contamination as it grew in human urine. To 100 mg of acrylamide absorbent polymer was added 5 ml of human urine (in a Petri plate) along with one *M. albus*-infested barley seed. A control plate with no *M. albus* was also set up. Contaminating fungi were supplied by the exposure of the plates to air and the acrylamide powder. After incubation for seven days at 23° C. the plates were assessed for fungal contamination by examination. In this case, the plates with *M. albus* did not possess any fungal contaminants, whereas the control plate was totally overgrown with *Penicillium* sp. (FIG. 6).

E. EXAMPLE 5

Antimicrobial Effects and Gas Production by *M. albus* in Human Urine and Solid Wastes An experiment was set up using 200 mg of acrylamide, 0.1 g of human feces, 0.9 ml of urine, and three barley seeds infested with *M. albus* in order to determine if *M. albus* grows in the presence of these ingredients (identical to those in the Phillips WAG BAG™), if volatile antimicrobial substances are produced, and what the effects of gas and other antibiotics are on the overall microbial population of the mixture. The mixture was placed in a Petri plate, and three infested barley seeds were placed on top of the dollop of wastes including the acrylamide polymer at room temperature. Growth of the *M. albus* was immediately noticed within 24 to 48 hours. After seven days the fungal growth was white and quite visible (FIG. 7). Bacterial populations were estimated by plating dilutions of weighed amounts of the human solid wastes on nutrient agar and then counting bacterial colonies under a binocular microscope after four days of incubation. A control Petri plate was also set up in which everything was comparable to the experimental plate except no fungus was added to the plate. After six weeks incubation of the fungus with the human wastes, there was a 50% reduction in the total bacteria that could be cultured from a sample of the waste. At the end of ten weeks, there was a 93% reduction in bacteria that could be cultured. The control plate had $70 \times 10^8$ bacterial colonies per mg of solid wastes, whereas the Petri plate with *M. albus* had only $4 \times 10^8$ colonies per mg of solid wastes.

An analysis of the gases in the environment of the Petri plates was done by GC/MS with the purpose of determining if *M. albus* was making any of its inhibitory volatiles in the presence of human wastes as contrasted to the control plate not having *M. albus*. The results showed that certain signature volatile antimicrobial compounds were produced by *M. albus* in the treated Petri plate, and these same compounds could not be detected in the control plate not containing *M. albus* (Table 2). It is to be noted that each of the compounds listed in Table 1, with the exception of propionic acid, 2-methyl-propyl ester, are also found in the atmosphere of *M. albus* grown on PDA as shown in Table 1. However, other esters of this same acid occur in *M. albus* culture atmospheres (depending upon the food base) including the methyl, ethyl, pentyl and 3-methyl butyl esters (Table 1). Propionic acid itself is a potent anti-microbial substance and can readily be released from the ester form via the action of commonly occurring esterases.

In addition to the Petri plate experiment with human wastes, we placed solid and liquid wastes in the WAG BAG™ in the presence of *M. albus* to determine if it would grow under the complete circumstances of being in the WAG BAG™. It turns out that the urine and other liquids wet the infested barley grain containing the culture of *M. albus* to a point that it is difficult to determine if fungal growth does occur. This problem was solved by examining the surface of the barley seed by scanning electron microscopy ten days after the WAG BAG™ had been buried in the soil under greenhouse conditions. FIG. 8 shows the standard appearance of the *M. albus* mycelium in growing on sterile plant material. Its interwound and ropy mycelium is characteristic of this fungus (Worapong et al., 2001). On barley seed, in the WAG BAG™ containing wastes, the fungus grows and produces small tufts of ropy mycelium on the surface of the barley seed comparable to that on other plant material (FIG. 9).

F. EXAMPLE 6

Preparation of *M. albus* for Placement in the WAG BAG™

A method is described for the preparation of *M. albus* for the placement into the WAG BAG™. Barley seed (approximately 100 g) is placed into a glass beaker to which is added an excess of water (until the added water is at least more than covering the seed). Then the container is placed in a microwave oven for ten minutes to facilitate the uptake of water into the seed. The excess water is decanted, and the moist seed is placed in a flask (with a stopper) and autoclaved for at least 40 to 60 minutes. This extended time is enough to kill all microorganisms associated with the seed. After an appropriate time for cooling, the flask containing the seed is inoculated with a fresh viable culture of *M. albus* and allowed to grow for at least one month at 23° C. (FIG. 10). Ultimately, the infested seed is removed from the flask and air dried in a sterile hood with sterile air. The air dried seed are then stored at −4° C. or at −70° C. or at room temperature. Fungus remains viable under these conditions of storage for at least nine months. In fact, infested seed stored at room temperature will also continue to support viable fungal growth for up to nine months.

REFERENCES

1. Bacon, C. W. and White, J. F., Jr. (2000). Microbial Endophytes. Marcel Dekker Inc. (New York).
2. Bjurman, J. and Kristensson, J. (1992). Mycopathologia 118: 173–78.
3. Dennis, C. and Webster, J. (1971). Trans. Br. Mycol. Soc. 57: 41–48.
4. Rapior, S., Fons, F. and Bessiere, J. (2000). Mycologia 92: 305–08.
5. Schnurer, J., Olsson, J. and Borjesson, T. (1999). Fungal Genetics and Biology 27: 209–17.
6. Strobel, G. A., Dirksie, E., Sears, J., and Markworth, C. (2001). Microbiol. 147: 2943–50.
7. Woropong, J., Strobel, G. A., Ford, E. J., Li, J. Y., Baird, G. and Hess, W. M. (2001). Mycotaxon. 79: 67–79.
8. Woropong, J., Strobel, G. A., Daisy, B., Castillo, U. F., Baird, G. and Hess, W. M. (2002). Mycotaxon. 80: 463–75.

DEFINITIONS

The term "esterase" means any of various enzymes that catalyze the hydrolysis of an ester.

The term "GC/MS" means gas chromatograph/mass spectrometer.

The term "hyphae" means any of the threadlike filaments forming the mycelium of a fungus.

The term "lignin" means a complex polymer, the chief noncarbohydrate constituent of wood, that binds to cellulose fibers and hardens and strengthens the cell walls of plants.

The term "mycelium" means the vegetative part of a fungus, consisting of a mass of branching, threadlike hyphae; or a similar mass of fibers formed by certain bacteria.

The term "PDA" means potato dextrose agar.

The term "room temperature" means 20° C. to 26° C.

The term "WAG BAG™" refers to a proprietary product that has been developed by Phillips Environmental Products, Inc. (PEP) of Belgrade, Mont. The WAG BAG™ is used in connection with PEP's Portable Environmental Toilet (PETT®).

The term "xylariaceae" refers to the family of fungi characterized by dark brown to black spores.

All other definitions set forth in the parent application (Ser. No. 10/121,740) are incorporated herein by reference. Please note that the term "effective amount," which is used in the claims, is defined in the parent application.

The invention claimed is:

1. A method of inhibiting the growth of and/or killing bacteria in human feces and/or urine comprising contacting the feces and/or urine with an effective amount of a culture of *Muscodor albus*, wherein the bacteria are selected from the group consisting of *Escherichia coli* and *Vibrio cholerae*.

2. The method of claim 1, further comprising:
   (a) infesting barley seed with *Muscodor albus;* and
   (b) adding the infested barley seed to the human feces and/or urine.

3. The method of claim 2, wherein the infested barley seed is added to the human feces and/or urine in a closed environment.

4. The method of claim 3, wherein the closed environment is a disposable bag.

5. The method of claim 4, wherein the disposable bag is used in connection with a portable toilet.

6. The method of claim 5, wherein the disposable bag is the WAG BAG™.

7. A method of inhibiting the growth of and/or killing bacteria in animal feces and/or urine comprising contacting the feces and/or urine with an effective amount of a culture of *Muscodor albus*, wherein the bacteria are selected from the group consisting of *Escherichia coli* and *Vibrio cholerae*.

8. The method of claim 7, further comprising:
(a) infesting barley seed with *Muscodor albus;* and
(b) adding the infested barley seed to the animal feces and/or urine.

9. The method of claim 8, wherein the infested barley seed is added to the animal feces and/or urine in a closed environment.

10. The method of claim 9, wherein the closed environment is a disposable bag.

11. The method of claim 10, wherein the disposable bag is used in connection with a portable toilet.

12. The method of claim 11, wherein the disposable bag is the WAG BAG™.

\* \* \* \* \*